United States Patent [19]

Maruo et al.

[11] Patent Number: 5,612,203
[45] Date of Patent: Mar. 18, 1997

[54] PROCESS FOR PRODUCING SACCHARIDES

[75] Inventors: Shigeaki Maruo, Osaka; Noriyuke Tachikake, Kyoto; Yohji Ezure, Shiga, all of Japan

[73] Assignee: Nippon Shinyaku Co. Ltd., Japan

[21] Appl. No.: 244,117

[22] PCT Filed: May 19, 1994

[86] PCT No.: PCT/JP92/01498

§ 371 Date: Aug. 8, 1994

§ 102(e) Date: Aug. 8, 1994

[87] PCT Pub. No.: WO93/10256

PCT Pub. Date: May 27, 1993

[30] Foreign Application Priority Data

Nov. 19, 1991 [JP] Japan ..................... 3-331212
Jan. 22, 1992 [JP] Japan ..................... 4-032569
Sep. 8, 1992 [JP] Japan ..................... 4-266639

[51] Int. Cl.[6] ............... C12P 19/04; C12P 19/12; C12P 19/14
[52] U.S. Cl. ............... 435/101; 435/100; 435/84; 435/85; 435/95; 435/96; 435/98; 435/99; 435/105; 536/124
[58] Field of Search ............... 536/124; 435/101, 435/84, 85, 95, 96, 98, 99, 100, 105

[56] References Cited

U.S. PATENT DOCUMENTS 4,622,295 11/1986 Ikenaka et al. ..................... 435/22
4,683,298 7/1987 Yalpani ..................... 536/45
4,713,118 12/1987 Barker et al. ..................... 127/38
4,787,939 11/1988 Barker ..................... 127/37

OTHER PUBLICATIONS

Kirk–Othmer Encyclopedia of Chemical Technology, vol. 13, 1981, pp. 678–705.
Robyt, et al, 145 Arch. Biochem and Biophysics 105–114 (1971).
Nakakuki, et al, 29 J. Jap. Soc. Starch Sci. 188–197 (1982).
Okemoto, et al, 25 Appl. Microbiol Biotechnol 137–142 (1986).

Primary Examiner—Michael G. Wityshyn
Assistant Examiner—Francisco C. Prats
Attorney, Agent, or Firm—Graham & James LLP

[57] ABSTRACT

Disclosed is a method for producing saccharides of definite chain length, such as glucose, maltose, malto-oligosaccharides and isomalto-oligosaccharides with a high purity. Saccharides such as starch, dextran and cellulose, and hydrolyzates thereof, are subjected to modification of the anomeric carbon at the reducing end of the molecule without modification of the non-reducing end of the molecule. The modification may be oxidation, for example by bromine to produce a carboxylic acid at the anomeric carbon, or amination, for example by phenylhydrazine to produce an osazone or osone of the saccharide. After modification, the modified saccharide can be adsorbed on an ion exchange resin and then repeatedly cleaved with a suitable enzyme, such as β-amylase, to produce the desired saccharide of definite chain length.

6 Claims, No Drawings

PROCESS FOR PRODUCING SACCHARIDES

FIELD OF THE INVENTION

This invention relates to a process for producing saccharides of definite chain length, such as glucose maltose, malto-oligosaccharides and isomalto-oligosaccharides with a high purity.

Among the saccharides of definite chain length which can be obtained by the process of the present invention, those having no branches include, inter alia, glucose and the species of the following formula:

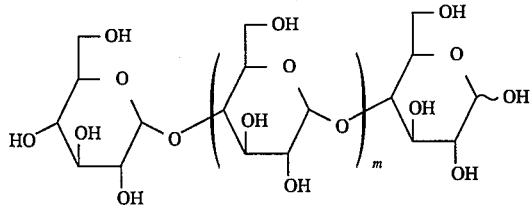

wherein m is an integer, m is preferably an integer of 0 to 5

Among such saccharides, maltose (m=0), maltotriose (m=1), maltotetraose (m=2), maltopentaose (m=3), maltohexaose (m=4) and the like can be used as pharmaceutical ingredients, food additives and starting materials for diagnostic reagents and so forth.

BACKGROUND OF THE INVENTION

Processes so far known for preparing high purity saccharides of definite in chain length generally comprise decomposing a saccharide having an arbitrary chain length, typically starch or the like, with one or more appropriate amylases and separating the object saccharide from the other unwanted oligo- and/or monosaccharides by the per se known column chromatographic and other fractionation techniques [cf. e.g. Jiro Nikuni (chief editor): Denpun Kagaku Handbook (Starch Science Handbook), published by Asakura Shoten, Tokyo, 1987, page 452] followed, if required, by crystallization of the object saccharide to further purify the same from the other unwanted contaminant oligo- and/or monosaccharides [cf. e.g. Denpun Kagaku Handbook (vide supra), page 456.].

However, these processes invariably entail formation of unwanted byproduct oligosaccharides in addition to uncleaved dextrin and, therefore, are inherently disadvantageous.

As regards maltose, a process for producing high-purity maltose from terrestrial starch has been proposed (Japanese Kokai Tokkyo Koho JP 04-158795). However, this process is still unsatisfactory from the commercial viewpoint since high concentration charging of starch is impossible.

For solving these and other problems, there has been made an invention which is disclosed in the international patent application PCT/JP91/00984 (International Publication No. WO 92/01805). According to the above invention, a saccharide chain is transferred from a saccharide chain source, either directly or via an intermediate, to a substance which can be substantially separated from the desired saccharide of definite chain length (such substance is hereinafter referred to briefly as separable substance) by means of a transglycosidase, then the thus-obtained saccharide is treated with an enzyme capable of excising a saccharide chain having a specific chain length from said saccharide in an exo manner (such enzyme is hereinafter briefly referred to as exo-cleaving enzyme), and finally the desired saccharide of definite in chain length is isolated.

In this connection, a mode of causing an exo-cleaving enzyme to act on amylose is described by Nakakuki et al. [T. Nakakuki, K. Azuma and K. Kainuma, Carbohydrate Research, 128 (1984) 297–310] and the application of the periodate oxidation technique, among others, is described by Marshall et al. [J. J. Marschall and W. J. Whelan, Analytical Biochemistry, 43 (1971) 316–321]. However, these technologies have no direct relevance to the whole technology of the present invention.

Althogh the process described in PCT/JP91/00984 is an absolutely novel process capable of solving a number of problems, it still has the following disadvantages.

(1) Since a transglycosidase is employed as an essential reagent and accordingly a saccharide chain source must be provided for the supply of the necessary saccharide chain, the yield of the object saccharide is inevitably poor.

(2) The use of a transglycosidase requires that said separable substance have a structure such that it can serve as a receptor for the transglycosidase (for instance, a substance whose hydroxyl groups in positions 2, 3 and 4 have a glucose-type configuration, or ascorbic acid or the like).

(3) After the formation of a desired saccharide of definite chain length by the action of an exo-cleaving enzyme, a procedure is essential for isolating said saccharide and, therefore, the yield is necessarily limited.

The object of the invention is to overcome the above technical drawbacks.

DESCRIPTION OF THE INVENTION

The present inventors made many investigations for overcoming these drawbacks and, as a result, found (1) that the above-mentioned object can be accomplished without using any transglycosidase, (2) that, hence, it is unnecessary to use any separable substance having a glucose type configuration and, further, (3) that when the treatment with an exo-cleaving enzyme is carried out on an ion exchange resin, the desired product can be isolated in a remarkably improved manner. Based on these and other findings, the inventors have now completed the present invention.

The present invention relates to a serial production process comprising subjecting a saccharide having an arbitrary chain length or a mixture of such saccharides to modification at the reducing end thereof, then treating the modification product with an enzyme capable of excising an saccharide chain of definite chain length in an exo manner to give a desired saccharide of definite chain length, and recovering said desired saccharide. In the practice of the present invention, no transglycosidase is employed.

The present invention further relates to a limitation of the above serial production process, wherein the starting material saccharides of arbitrary chain length are modified as above and, then, adsorbed on an ion exchange resin before being treated with an exo-cleaving enzyme.

The modification as used herein means derivatization, by chemical treatment of the reducing end, of a starting material into a compound (e.g. compound A, B, C, D or E mentioned later herein) isolatable by a simple isolation procedure such as ion exchange resin treatment, solvent extraction, filtration or centrifugation. This modification includes those cases in which a certain specific functional group is introduced into the reducing end group from an external source by a chemical reaction and those cases in which a partial structure of the reducing end is converted to a functional group.

Reducing end as used herein means the anomeric carbon position which is the position 1 of the monosaccharide at the terminal of a saccharide such as said saccharide having an arbitrary chain length.

Since, generally, a monosaccharide having such an anomeric carbon position is sometimes referred to as a reducing end, a monosaccharide having a reducing end is also referred to as the reducing end in this specification as well.

In accordance with the invention, the substance corresponding to the separable substance so referred to in the above-cited prior art publication (International Publication WO92/01805) can be obtained by using a compound capable of modifying the reducing end of a saccharide (hereinafter referred to as "reducing end modifier").

In the practice of the invention, the reducing end modification can be performed, for example, by oxidizing the reducing end of the starting saccharide(s) or introducing a substituted or unsubstituted amino group into said end.

As the substituent or substituents of such substituted amino group, there may be mentioned substituted or unsubstituted alkyl groups, substituted or unsubstituted aryl groups, and the like.

In accordance with the invention, ion exchange resins can be used efficiently to produce the effects of the invention.

In that case, the starting saccharide(s) after reducing end modification can be adsorbed on an ion exchange resin. After this adsorption step, the resin is washed by a per se known method, by which the saccharide(s) modified at the reducing end in accordance with the invention can be retained alone within the ion exchange resin via ionic bonding. Thereafter, the modified saccharide(s) can be reacted with an exo-cleaving enzyme in accordance with the invention. Then, the desired saccharide of definite in chain length as formed within the ion exchange resin can be recovered by a simple procedure such as washing or elution.

By following the above-mentioned serial procedure according to the invention, it is possible to conduct the step of isolating the desired product after production thereof in accordance with the invention in a very simple and easy manner. In addition, it is also possible to obtain the desired product with a very high purity.

In the following, the invention is described in further detail.

In the practice of the invention, a saccharide having an arbitrary chain length is used as the starting material.

Preferred examples of such saccharide are seed starch, root starch, chemically modified starch and the like starch species.

The chemically processed starch includes not only such chemically processed starch species as acid-treated starch, oxidized starch, crosslinked starch, esterified starch, etherified starch and graft-copolymerized starch but also physically processed starch species such as wet heat-treated starch and α-starch, enzymatically modified starch species such as dextrin, amylose and high-content amylose, and so forth.

As an important class of such saccharides as mentioned above, there may be mentioned saccharides having glucose units joined by α-1,4-glycosidic bonds. Saccharides involving α-1,6-bonding are also applicable and, further, saccharides having β-1,4-bonding can also be used.

When a saccharide having α-1,4-bonding, for example starch, is treated with such an exo-cleaving enzyme as mentioned later herein, for example β-amylase, in accordance with the invention, a malto-oligosaccharide is obtained as the final product.

When a saccharide having α-1,4-bonding, for example starch, is treated with such an exo-cleaving enzyme as mentioned later herein, for example glucoamylase, in accordance with the invention, a glucose is obtained as the final product.

When a saccharide having α-1,6-bonding, for example dextran, is treated with an exo-cleaving enzyme such as isomaltodextranase in accordance with the invention, an isomalto-oligosaccharide such as isomaltose is obtained as the final product.

When a saccharide having β-1,4-bonding, for example cellulose, is treated with an exo-cleaving enzyme such as cellulase in accordance with the invention, a cello-oligosaccharide such as cellobiose is obtained as the final product.

The product to be obtained by the process of the invention can be selected by employing an appropriate one selectively from among the exo-cleaving enzymes mentioned later herein.

The above-mentioned starting saccharide(s), which may have any chain length, may be straight-chained or branched. A mixture of straight-chained and branched saccharides may also be used.

As such saccharides, there may be mentioned, for example, seed starch, root starch, chemically processed starch, dextrin, and mixtures of these.

Products of liquefaction of such starch species as mentioned above by means of α-amylase or the like, products of such liquefaction followed by treatment with a debranching enzyme such as pullulanase or isoamylase, and thick malt syrup or the like are further examples of said saccharides. Such liquefaction can be effected by adding a uni- or polyvalent metal hydroxide or salt or the like, such as sodium hydroxide, potassium hydroxide, sodium carbonate, sodium hydrogen carbonate, potassium carbonate, potassium hydrogen carbonate, calcium hydroxide, calcium carbonate, calcium chloride, barium hydroxide, barium carbonate, barium chloride, aluminum hydroxide or aluminum chloride.

Amylose, maltopentaose, other malto-oligosaccharides, and mixtures of these may also be recommendable as being appropriate as said saccharides.

In the practice of the invention, mixtures of those saccharides mentioned above may further be used.

The oxidized starch mentioned hereinabove as a kind of chemically processed starch can be used as the starting material in the process of the invention but does not include any saccharide after that oxidation treatment which is one of the reducing end modification methods to be employed in the practice of the invention [Jiro Nikuni (chief editor): Denpun Kagaku Handbood, Asakura Shoten, 1987, page 501; Doutoku Nakamura and Keiji Kainuma (editors): Denpun Kanren Toushitsu Jikken-ho (Experiments with Starch-Related Carbohydrates), Asakura Shoten, 1989, page 298; Hiromichi Kato et al.: Shin Nousanbutsu Riyou-gaku (New Uses for Agricultural Produces), Asakura Shoten, 1987, page 35).

The process of this invention which uses the above-mentioned saccharide having an arbitrary chain length is further described below with regard to several representative types of reducing end modification. It is to be noted, however, that these types are by no means limitative of the scope of the present invention.

[Reducing end modification type I-(1)]

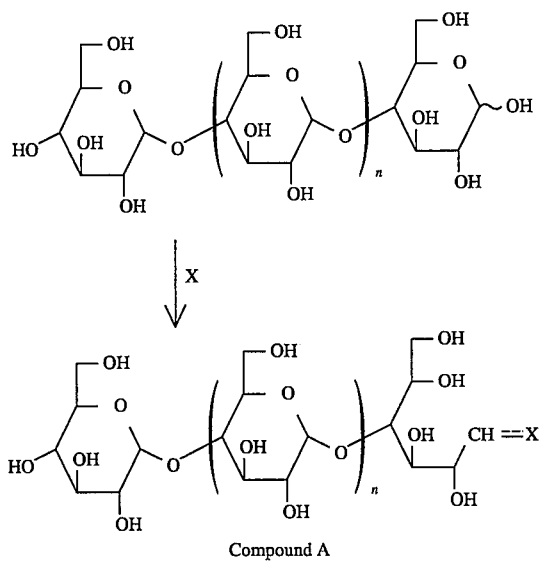

Compound A

⁓⁓⁓ means single bond or double bond, n is an integer greater than m.

In practicing the invention, a reducing end modifier X may be first coupled to the starting saccharide.

Said reducing end modifier may be any of those compounds that can react with the reducing end of the starting saccharide. While typical examples will be given later herein, mention may now be made of, for example, compounds which can react with the reducing end of the starting saccharide and have a basic or acidic functional group.

In the practice of the invention, compound A capable of being adsorbed on an ion exchange resin, for instance, can be produced using such reducing end modifier.

As said reducing end modifier, there may be mentioned amino-containing compounds. Typical examples are phenylhydrazine, 2,4-dinitrophenylhydrazine, other substituted phenylhydrazines, semicarbazones, hydroxylamine, amines such as alkylamines which may optionally be substituted, and alkylamines or other amines which have a phenyl group which may optionally be substituted.

In addition to those mentioned above, compounds having a heterocyclic and a functional group reactive with aldehydes, for example 2-aminopyridine, may also be mentioned as the reducing end modifier to be used in the practice of the invention. Amine donors in some other form, for example ammonium acetate, may also be used.

In the above reaction, a compound well known in the art as the so-called Schiff base is generally formed. The double bond of the Schiff base can be converted to a single bond to give a more stable compound by adding sodium borohydride, sodium cyanoboro-hydride or the like to the reaction system during the reaction. It is also possible to reduce the Schiff base once formed by hydrogenating using an appropriate catalyst such as Raney nickel or palladium-carbon.

[Reducing end modification types I-(2) and I-(3)]

When the reducing end modifier is a macro-molecule in type I-(1), the present invention can be practiced in the following manner. In this case, the subsequent isolation procedure can be facilitated by employing a simple procedure such as filtration.

an example of I-(2)

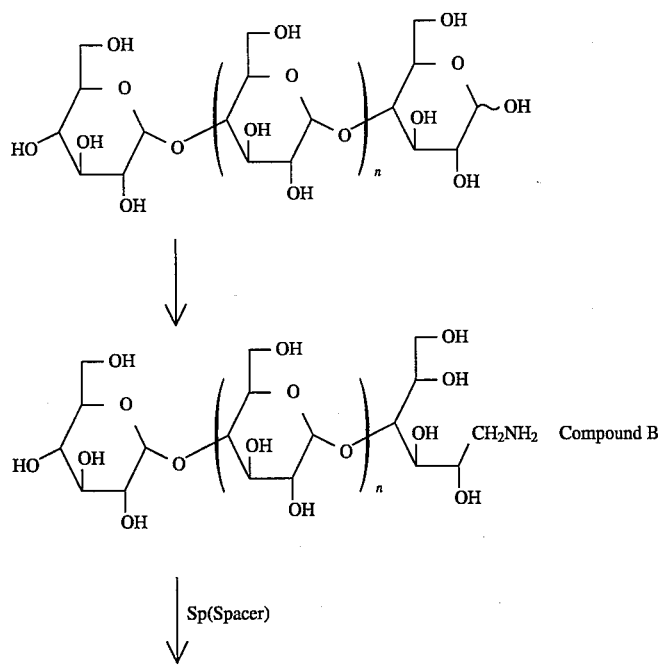

-continued

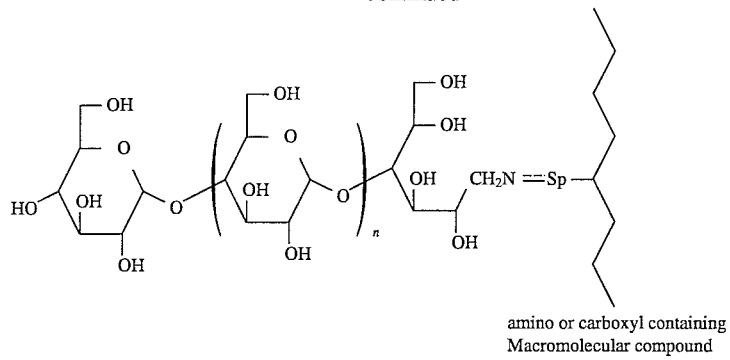

amino or carboxyl containing
Macromolecular compound an example or 1-(3)

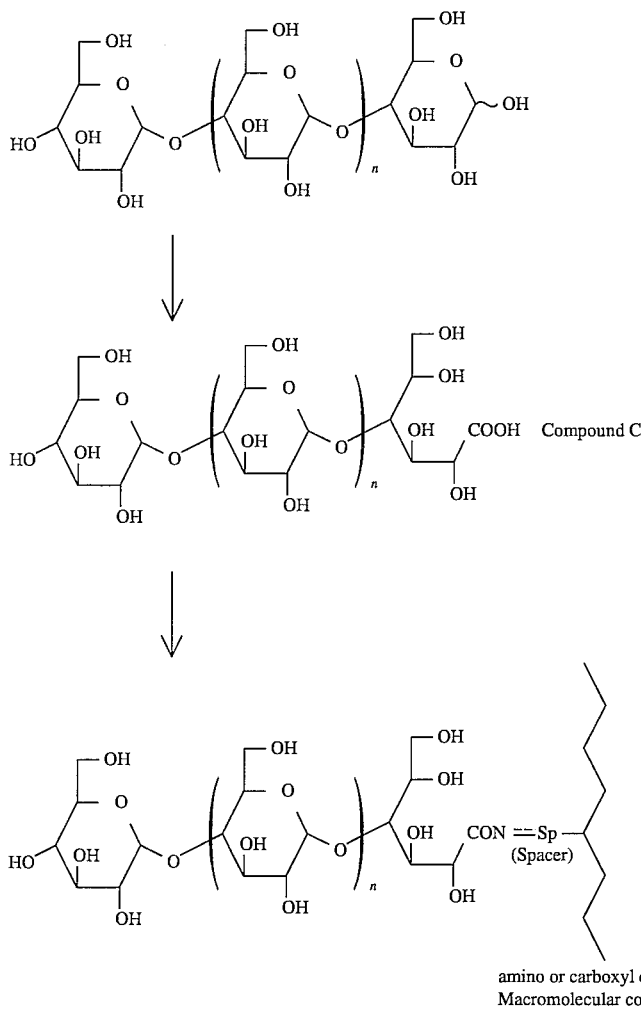

Compound C amino or carboxyl containing
Macromolecular compound

In the practice of the invention, the starting saccharide can be derived into Compound B having basicity by reacting said saccharide with such a reducing end modifier as a cyanoborohydride or ammonium acetate.

Then, Compound B is chemically bound to a macromolecular compound (e.g. a weakly basic ion exchange resin) using, for example, the so-called bifunctional spacer, such as glutaraldehyde or 1,4-butanediol diglycidyl ether [type I-(2)].

In the practice of the invention, the starting saccharide can be derived into compound C having acidity by reacting said saccharide with such a reducing end modifier as bromine, chlorine, aqueous bromine, hypoiodous acid, hypochlorous acid, bleaching powder or hydrogen peroxide.

The oxidation in this case can be carried out in the same manner as the oxidation to be described later herein in detail regarding type III.

Then, Compound C can be chemically bound to an amino-containing macromolecular compound such as ω-aminoalkylamine-agarose using a water-soluble carbodiimide as a condensing agent [type I-(3)].

When the macromolecule-bound Compound C is then treated with an exo-cleaving enzyme, the desired product can be isolated by mere filtration.

In chemically binding the saccharide to the macromolecular compound in the above case, the macromolecular compound may be activated in advance (e.g. epoxy-activated acrylamide, epoxyactivated Sepharose) and then reacted with Compound C.

Said macromolecular compound may be either a water-insoluble compound or a water-soluble compound having a molecular weight of several thousand to scores of thousands. In the latter case, the object can be attained by ultrafiltration.

It is not necessary to react all functional groups in each molecule of the macromolecular compound with a spacer or the like. If some polar functional groups are retained, particularly when the macromolecule is soluble in water or the like, these polar functional groups can favorably be utilized for product separation using an ion exchange resin, for instance.

The following methods of reducing end modification of saccharides can further be mentioned.

The object of the invention can be achieved also after deriving the reducing end aldehyde of the starting saccharide into a nitrile-containing compound such as a cyanhydrin, then deriving said compound into an amino-containing compound by reduction. The object of the invention may further be accomplished using the starting saccharide in the form of a hydrosulfite adduct obtained by derivatization from the aldehyde using a hydrosulfite salt or the like or in the form of a sulfo-containing compound derived from such adduct.

Reducing end modification type II]

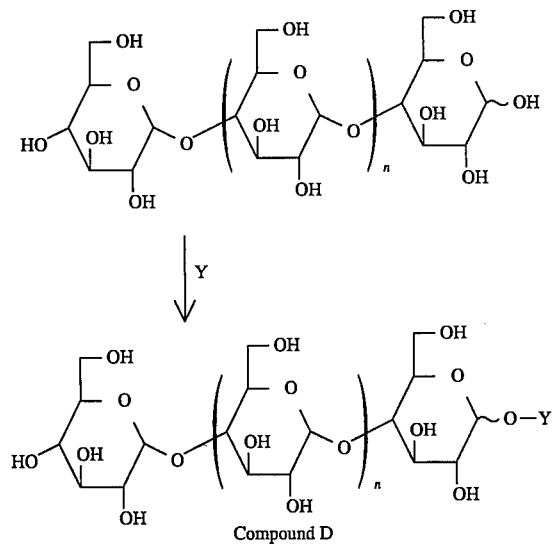

Compound D

Another type can be mentioned which can be used in the practice of the invention. As such, there may be mentioned the use, as the reducing end modifier, of a lower alkyl alcohol or phenol derivative, which may optionally be substituted.

Such lower alkyl alcohol or phenol derivative, which may optionally be substituted, must have a basic functional group such as an amino group, or an acidic functional group such as a sulfo or carboxyl group. (The functional group may suitably be protected.)

Reaction of such compound, as the reducing end modifier, with the hydroxyl group in the anomeric carbon position can give the desired Compound D. In this reaction, an inorganic acid, a Lewis acid, a cation exchange resin or the like can be used as an acid catalyst. When the reducing end modifier used has a protective group, Compound D can be obtained by deprotecting the modification product.

Acylation of the reducing end is another example and comprises reacting the starting saccharides with an acid anhydride or acid halide in the presence of an acid or base catalyst. Where the acid anhydride or the like has an appropriately protected amino group, compound D can be obtained by deprotection following acylation.

The reaction between the starting saccharide and the reducing end modifier in the practice of the invention can be carried out in the same manner as in ordinary chemical reactions of the same type. The reaction temperature, reaction time and other conditions can be arbitrarily selected and applied so that they can be optimum for the reaction applied. For isolating the reaction product, such a general technique as pH adjustment, centrifugation, precipitation or filtration can suitably be applied.

[Reducing end modification type III]

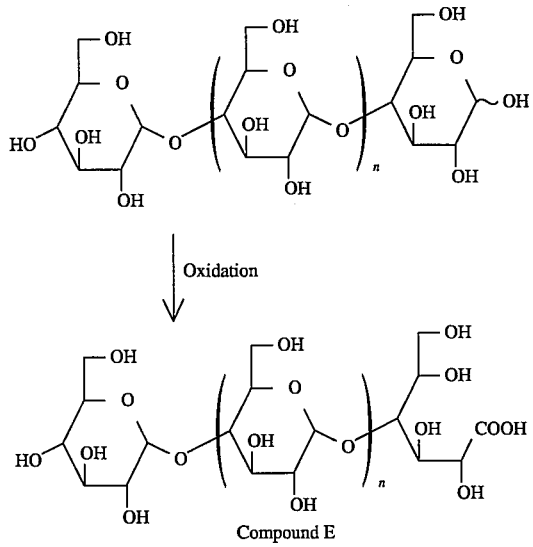

Compound E

In the practice of the invention, the reducing end of the starting saccharide can be converted to a carboxylic acid by oxidation of the anomeric carbon position of the saccharide to give compound E. Such oxidation can be carried out using such an oxidizing agent as hypohalous acid such as hypoiodous acid, hypochlorous acid and hypobromous acid, hypohalite such as sodium hypobromite, sodium hypochlorite, sodium hypoiodite, potassium hypobromite, potassium hypochlorite, and potassium hypoiodite, bromine, chlorine, iodine, bleaching powder or hydrogen peroxide, or the like.

Among the oxidizing agents mentioned above, bromine, chlorine, hypohalite such as sodium hypoiodite, sodium hypochlorite and sodium hypobromite are preferred.

The oxidation can also be carried out by adding chlorine, bromine or iodine into the reaction mixture. In this case, the pH of the reaction mixture is not critical but, considering the stability of the starting saccharide, such as starch, and the efficient reactivity of chlorine, bromine or iodine, it is preferable to add chlorine, bromine or iodine into the reaction mixture while said mixture is kept alkaline using sodium hydroxide, potassium hydroxide, calcium hydroxide, barium hydroxide or the like.

In the practice of the invention, the above oxidation can also be carried out in the manner of air oxidation using a catalyst such as palladium carbon.

In such oxidation, a buffer such as barium carbonate may suitably be caused to coexist in the reaction mixture.

The above oxidation can also be performed in the manner of electrolytic oxidation, or biological oxidation using a microorganism having aldose dehydrogenase activity or using aldose dehydrogenase.

Periodic acid oxidation is not suited for the practice of the invention since periodic acid shows a strong tendency toward simultaneous oxidation of other portions rather than the reducing end.

[Reducing end modification type IV]

A further type which does not belong to any of the above-mentioned types may be mentioned.

In the practice of the invention, the starting saccharide can be converted to a separable substance having a polar group for use in the process of the invention, for example a phosphate ester, by O-acetylating the position 1 of the reducing end and treating the acetylation product with a hydrogen halide to give a halide having one substituent halogen atom, followed by further derivatization from this compound.

Furthermore, the starting saccharide can be derived into a separable substance having a polar group for use in the process of the invention by converting the reducing end of said saccharide to a glycal, followed by further derivatization therefrom. Such substance does not fall within any of the compound categories A, B, C, D and E mentioned above as representative types of reducing end modification in the process of the invention.

The reducing end modification reaction in the practice of the invention can be performed according to the types I to IV mentioned above.

In the practice of the invention, the above-mentioned reducing end modification reaction can be immediately followed by treatment with an exo-cleaving enzyme. Conceivable as such case are, for instance, cases where contamination of the final product with a small amount of other oligosaccharides than the desired one and/or a small amount of the starting saccharide(s) that has not subjected to the reducing end modification reaction is allowable, and cases where the reaction conditions in the process of the invention are so suitable that the object of the invention can be attained without performing any particular purification treatment.

In the practice of the invention, after the above reducing end modification reaction, a separation procedure paying attention to the polar functional group may be applied prior to treatment with an exo-cleaving enzyme.

Thus, for instance, in the case of the above-mentioned Compound A, D or E, the unreacted excess reagent can be removed using an organic solvent or by such means as dialysis, and/or desalting treatment or the like may be performed, when necessary.

When necessary in the above-mentioned reducing end modification type I-(1), for instance, such treatment as mentioned above can be conducted using an ion exchange resin. As such ion exchange resin, there may be mentioned those examples given later herein.

In the practice of the invention, the reducing end modification reaction is followed, with or without the above measure (separation procedure paying attention to the polar functional group), by the step of treatment with an exo-cleaving enzyme, as is evident from the foregoing description.

In the practice of the invention, the treatment with an exo-cleaving enzyme can be conducted at a pH suited for the exo-cleaving enzyme.

The kind of the exo-cleaving enzyme can suitably be selected depending on the desired product saccharides of definite in chain length.

The level of addition of the exo-cleaving enzyme can suitably be selected depending on the kind of said enzyme and other factors.

The reaction temperature and reaction time can suitably be varied depending on the kind and amount of the enzyme employed.

In the step of exo-cleaving enzyme treatment, the exo-cleaving enzyme can be caused to act on the terminally modified saccharide in the presence of another enzyme such as pullulanase, isoamylase or β-amylase.

As typical examples of the exo-cleaving enzyme to be used in the practice of the invention, there may be mentioned glucoamylase, β-amylase and malto-oligosaccharide forming enzymes, among others.

Such exo-cleaving enzymes are described below in further detail. As a maltotriose forming enzyme, there may be mentioned, among others, the enzyme described in Denpun Kagaku, 25, 155–161 (1978) as derived from *Streptomyces griseus* NA-468 (FERM-2227).

As a maltotetraose-forming enzyme, there may be mentioned, among others, the enzyme described in Arch. Biochem. Biophys., 145, 105–114 (1971) as derived from several strains of *Pseudomonas stutzeri* or the enzyme described in the Abstracts of Papers Presented at the 1985 Annual Meeting of the Agricultural Chemical Society of Japan, page 370, as derived from *Pseudomonas saccharophila* IAM 1504.

As a maltopentaose forming enzyme, there may be mentioned, among others, the enzyme described in the Abstracts of Papers Presented at the 1984 Annual Meeting of the Agricultural Chemical Society of Japan, page 181, as derived from Pseudomonas KO-8940 (FERM P-7456).

As an isomaltose-forming enzyme, there may be mentioned, among others, isomalto dextranase. As a cellobiose forming enzyme, there may be mentioned, among others, cellulase.

For producing maltose, for instance, β-amylase can be used. It is recommended that the reaction system is adjusted to a pH level suited for β-amylase, namely pH 4 to 10, preferably pH 7.6, then β-amylase added to the reaction system and the mixture incubated at a reaction temperature of 25° to 65° C. for several hours to 2 days. When a maltotetraose-forming enzyme is used, the intended object can be accomplished by carrying out the reaction at a pH level suited for the maltotetraose-forming enzyme, namely at pH 4 to 10, preferably pH 8.0, and at a temperature of 25° to 55° C. for several hours to 2 days.

The exo-cleaving enzyme can be recovered for reuse thereof.

The exo-cleaving enzyme can be used either in a solution form or in the form of an immobilized enzyme prepared by a per se known enzyme immobilization method in general use. In particular when the enzyme to be used is a crude one, its use in an immobilized form can contribute to reduce the level of contamination and therefore is advantageous from the purification viewpoint.

In accordance with the invention, the desired saccharide of definite chain length can be isolated substantially alone by treating the exo-cleaving enzyme treatment mixture by means of an ion exchange resin or an electrodialyzer.

When an ion exchange resin is used for the purpose of isolating the desired product after exo-cleaving enzyme treatment in the process of the invention, the reaction mixture is charged onto the ion exchange resin and this resin is washed thoroughly, whereby the desired product can be recovered from the washings. Ion exchange resin treatment can also serve as desalting treatment and/or the like simultaneously.

The ion exchange resin to be used in the practice of the invention may be an acidic ion exchange resin or a basic ion exchange resin as the occasion demands. As such resin, there may be mentioned, for instance, Dowex 50WX2 (registered trademark), Dowex 1X2 (registered trademark), Dowex SBR (registered trademark), Dowex 66 (registered trademark), Diaion SK-104 (registered trademark), Diaion SA-11A (registered trademark), Diaion WK20 (registered trademark), Diaion WA20 (registered trademark), Diaion CR10 (registered trademark), Diaion PA306 (registered trademark), Diaion PA406 (registered trademark), Amberlite IR-120 (registered trademark) and Amberlite HFS-471X (registered trademark). The amount of such ion exchange resin can be increased or decreased if necessary.

In the practice of the invention, the step of exo-cleaving enzyme treatment in the above-mentioned serial process can be performed in a state in which the reducing end-modified saccharide is adsorbed on an ion exchange resin.

This modified process has been established based on the finding obtained in the course of sophisticating the steps involved in the above-mentioned serial process of the invention, that the exo-cleaving enzyme reaction can proceed very successfully in an ion exchange resin layer.

This modified process, which constitutes an embodiment of the invention, can eliminate the steps (2) and (4) of the above-mentioned serial process comprising the steps of (1) reducing end modification of the starting saccharide, (2) purification, (3) the exo-cleaving enzyme reaction and (4) purification while allowing the step (3) to be carried out on an ion exchange resin.

According to said modified process, the starting saccharide terminally modified by the above-mentioned reducing end modification reaction can be adsorbed on an ion exchange resin. As examples of said ion exchange resin, there may be mentioned those given herein before.

The resin can be washed with water or the like.

In this step of said process, the unmodified saccharide remaining as a contaminant for such reasons as insufficient progress of the reducing end modification reaction is not adsorbed on the ion exchange resin but is separated and eluted. Therefore, starting material purification can be finished in a very simple and easy manner. This is one of the surprising effects of said process.

In said process, the enzymatic reaction can then be caused to proceed by passing the exo-cleaving enzyme mentioned above through the ion exchange column.

In said process, the desired substance can be separated by means of the ion exchange resin even in the course of the exo-cleaving enzyme reaction since it is a neutral substance. More preferably, the desired product can be recovered by thoroughly washing the resin after completion of the exo-cleaving enzyme reaction.

Said modified process can simplify the process of the invention as a whole and, in addition, increase the purity of the desired product formed.

In all the production processes according to the invention as disclosed herein, inclusive of the above-mentioned modified process, each purification step can be conducted using an appropriate combination of per se known techniques.

Thus, for instance, when exo-cleaving enzyme treatment is performed immediately after completion of the reducing end modification reaction, such techniques as filtration, active carbon treatment, ultrafiltration and desalting can be applied following the exo-cleaving enzyme treatment.

For removing those reducing end-modified saccharide fragments that remain in cleaved form after exo-cleaving enzyme treatment, any appropriate combination of such treatment means as electrodialyzer, ion exchange resin treatment, concentration, recrystallization and drying.

When, for instance, the mixture obtained after completion of the reaction for reducing end modification of starch is subjected to such separation procedure paying attention to the polar functional group as filtration and ion exchange resin treatment prior to exo-cleaving enzyme treatment, it is possible to treat the reaction mixture obtained after the separation procedure with an exo-cleaving enzyme and then remove, from the reaction mixture, those reducing end-modified saccharide cleavage fragments which remain after exo-cleaving enzyme treatment by means of an electrodialyzer or ion exchange resin, for instance, followed by application of such treatments as active carbon treatment, filtration, concentration, recrystallization and drying, selected and combined in an appropriate manner, as necessary.

In such purification procedure, when, for instance, the starting saccharide is derived into an acidic substance by reducing end modification, such steps as adding calcium hydroxide, barium hydroxide or the like to the reaction mixture and concentrating the resulting mixture to thereby precipitate most of those reducing end-modified saccharide cleavage fragments which remain after exo-cleaving enzyme treatment may be incorporated for the purpose of reducing the amount of ion exchange resin and/or other materials required for the subsequent treatment or for the purpose of facilitating electrodialyzer treatment.

In such purification procedure, when, for instance, an oxidizing agent such as sodium hypochlorite is used for reducing end modification of the starting saccharide, it is possible, when necessary, to inactivate the excess oxidizing agent using a reducing agent such as sodium sulfite and then apply the above-mentioned purification means.

When a hydrophobic compound is involved in the reducing end modification reaction, it is possible to incorporate such means as organic solvent extraction.

The present invention not only imparts the advantage that saccharide of definite chain length alone can be obtained but also markedly simplifies the production process as compared with the prior art processes, sharply reducing the cost and labor and satisfactorily increasing the yield.

Among the saccharides obtainable by the process of the present invention, glucose or maltose, for instance, is particularly suited for pharmaceutical uses where a high purity is required, for example in the case of drip infusion fluids.

They are of course useful in the field of food industry. Maltose is of very high value in said field where a high purity is required as in the pharmaceutical field. Here is thus found one of typical fields of application of the production process of the present invention.

Among the saccharides obtainable by the process of the invention, maltotriose (m=1), maltotetraose (m=2), maltopentaose (m=3), maltohexaose (m=4) and the like can be used as starting materials for diagnostic reagents.

Maltose, when prepared by the process of the invention, is very effective in producing maltitol, a sweetening agent, by reduction of maltose since the use of purer maltose as the starting material results in better crystallization of maltitol.

Maltotetraose, maltopentaose and the like are also useful as ingredients of enteral feeding compositions [Shokuhin Kogyo (Food Industry), Aug. 30, 1990 issue, page 52].

In the pharmaceutical field, the saccharides prepared by the process of the invention can be used, for example, in infusion fluid compositions. When employed in infusion fluids, maltose gives an isotonic solution at a concentration of 10% and has a caloric value twice higher as compared with an equal amount of glucose and, for these and other reasons, maltose is known to be more beneficial than glucose or the like [Masui to Sosei (Anesthesia and Resuscitation), 20 (3), 163 (1984)]. Similarly, a 15% maltotriose solution, which is isotonic, is three times higher in caloric value as compared with glucose, hence is still more efficient.

In applying the saccharides produced by the process of the invention to the pharmaceutical field, the formulation given later herein as an infusion fluid composition, for instance, may be employed. Generally, infusion fluids may contain the saccharide (maltotriose, maltotetraose, maltopentaose, maltohexaose, etc.) either alone or in combination with glucose and/or maltose, together with inorganic salts, such as sodium chloride, potassium chloride and sodium acetate, each in an appropriate amount.

In the practice of the invention, when an oxidizing agent is used for the above-mentioned reducing end modification reaction, the reaction is carried out generally at a temperature of 50° C. or below. It is also possible, however, to conduct the reaction at a temperature higher than 50° C. or, if necessary, at a temperature of 90° C. to 100° C. or still higher, for a shortened period of time.

At high temperatures, the reaction velocity is high although the oxidizing agent is decomposed rapidly. Therefore, in practicing the invention on a commercial scale, it is possible to conduct the reaction continuously in a pipeline such as a continuous liquefying apparatus and a continuous saccharifying apparatus, for example by adding the oxidizing agent to the pipeline while a solution containing liquefied starch, starch milk or the like prepared in accordance with the invention is passed therethrough at a high temperature.

When such an oxidizing agent as sodium hypochlorite or calcium hypochlorite, for instance, is used, the construction material of the reaction vessel is limited because of the oxidizing action of the oxidizing agent and, in some instances, reaction vessels made of a material generally used in the starch industry or the like may be inadequate. However, when the reaction mixture obtained by conducting the reaction in a pipeline is continuously poured into the reaction vessel in which the next reaction step such as debranching enzyme treatment or saccharification reaction, said next reaction can be performed in an ordinary reaction vessel since, if the oxidation is complete in the pipeline, the oxidizing agent or the like is mostly consumed while its passage through the pipeline. In this case, the reaction within the pipeline can be conducted within a broad reaction temperature range by selecting the pipeline length so as to be appropriate for the reaction temperature. Furthermore, when an adequate pipeline material is selected, the pipeline can be prevented from corrosion by the oxidizing agent; this is advantageous from the equipment cost, maintenance cost and other viewpoints.

The present invention makes it possible to produce the following effects.
(1) The desired products can be obtained in very good yields since no transglycosidase is used.
(2) Various saccharide materials, such as seed starch, root starch, chemically processed starch, dextrin, oligosaccharides, and mixtures of these can be widely used as starting materials.
(3) Those high-purity products that cannot be produced by the prior art liquefaction/saccharification processes can be obtained, and that in improved yields.
(4) The purification steps can be simplified.
(5) Since starch after reducing end modification has a low viscosity, it is now possible to submit, on a commercial scale, high-concentration starch to the enzymatic reaction; this leads to improved productivity and cost reduction.
(6) When, for instance, corn starch, which produces marked turbidity particularly at high concentrations, is used as the starting material, reducing end modification causes a decrease in turbidity and an increase in solubility so that the subsequent purification step can be simplified.
(7) Such food additive as sodium hypochlorite can be used as the oxidizing agent for use in reducing end modification by oxidation. This is very suited for the production of desired products to be used in foods.

EXAMPLES

The following examples illustrate the invention in further detail.

EXAMPLE 1

Maltopentaose (200 mg, at least 98% pure, obtained from Seikagaku Kogyo) was dissolved in 20 ml of distilled water, 4 ml of a phenylhydrazine solution (phenylhydrazine:acetic acid:water=2:1:1 by volume), and the mixture was heated on a boiling water bath for 90 minutes, then allowed to cool, made weakly alkaline (pH 8.65) by additon of 16.5 ml of 1M sodium carbonate and extracted three times with an equal volume of ethyl acetate. The aqueous layer was desalted with a bench-top desalting apparatus (Asahi Chemical Industry Microacilyzer Model G1) using a separating membrane of Aciplex cartridge AC-220-10. The volume of the treated liquid was 21.3 ml. The formation of the maltopentaose osazone and the disappearance of the starting material maltopentaose were confirmed by thin layer chromatography (TLC) using a silica gel 60F$\beta_{45}$ plate (Merck; developing solvent: 1-propanol:ammonia:water=6:1:2 by volume). Unless otherwise specified, the "TLC" or "TLC analysis" referred to hereinafter was performed in the same manner in every case.

To the above maltopentaose osazone solution (21.3 ml in volume, pH 9.2) was added 6,658.5 units (6.9 mg as protein) of $\beta$-amylase (EC 3.2.1.2; obtained from Sigma Chemical Company; derived from sweet potato), and the resultant mixture was incubated at 40° C. for 60 minutes. After confirmation of maltose formation by TLC, the mixture was ice-cooled and the resultant precipitate was removed by centrifugation (14,250 G×15 minutes). The supernatant was diluted to a volume of 100 ml with distilled water and the dilution (pH 7.08) was applied to a column (25 mm $\phi$×50 cm) packed with 100 ml of a strongly acidic ion exchange resin (Dowex 50WX2, H$^+$ form). The effluent fraction was regarded as an unadsorbed fraction. The column was washed with water and the eluate was fractionated in 100-ml portions. Each fraction was evaporated to dryness under reduced pressure, the resultant solid was dissolved in 1 ml of distilled water, and the solution was subjected to TLC analysis. In this way, it was found that the effluent fraction and the first 100 -ml eluate fraction contained the desired product maltose. These fractions were combined and concentrated to 5.0 ml. Methanol (1.2 ml) and 40 mg of active carbon (Darco G-60, Wako Pure Chemical Industries) were added to the concentrate, and the mixture was incubated at 50° C. for 30 minutes. The active carbon was removed by centrifugation (14,250 G×15 minutes) and the supernatant was evaporated to dryness under reduced pressure, whereby 53.4 mg of maltose was obtained. The yield was 66.8%. Upon TLC analysis, this product gave a single spot.

EXAMPLE 2

Amylose A (200 mg; obtained from Nakalai Tesque; derived from corn starch, average molecular weight about 2,900) was dissolved in 20 ml of distilled water with heating, 4 ml of a phenylhydrazine solution (phenylhydrazine:acetic acid:water=2:1:1 by volume) was added, and the resultant mixture was heated on a boiling water bath for 90 minutes. The mixture was then allowed to cool, adjusted to pH 9.25 by addition of 13.0 ml of 1M sodium carbonate and extracted three times with an equal volume of ethyl acetate. The aqueous layer was desalted with a bench-top desalting apparatus(Asahi Chemical Industry Microacilyzer Model G1) using a separating membrane of Aciplex cartridge AC-220-10. The volume of the treated liquid was 29.8 ml. β-Amylase (EC 3.2.1.2; obtained from Sigma; derived from sweet potato) (6,658.5 units, 6.9 mg as protein) was added to that amylose A osazone solution (pH 7.57), and the mixture was incubated at 40° C. for 60 minutes. After confirmation of maltose formation by TLC, the mixture was ice-cooled and the resultant precipitate was removed by centrifugation (14,250 G×15 minutes). The supernatant was diluted to a volume of 100 ml with distilled water, and the dilution (pH 6.96) was applied to a column (25 mm φ×50 cm) packed with 100 ml of a strongly acidic ion exchange column (Dowex 50WX2, H$^+$ form). The effluent fraction was regarded as an unadsorbed fraction. The column was washed with water and the eluate was fractionated in 100 ml portions. Each fraction was treated with the above-mentioned Microacilyzer, then evaporated to dryness under reduced pressure and dissolved in 1 ml of distilled water, and the solution was subjected to TLC analysis, whereby it was found that the effluent fraction and the first 100 ml eluate fraction contained the desired product maltose. These fractions were combined and concentrated to 5.0 ml, 1.2 ml of methanol and 40 mg of active carbon (Darco G-60, obtained from Wako Pure Chemical Industries) were added to the concentrate, and the mixture was incubated at 50° C. for 30 minutes. The active carbon was removed by centrifugation (14,250 G×15 minutes and the supernatant was evaporated to dryness under reduced pressure, whereby 123.5 mg of maltose was obtained. The yield was 69.5%. Upon TLC analysis, this product gave a single spot.

EXAMPLE 3

Maltopentaose (300 mg, obtained from Seikagaku Kogyo, at least 98% pure) was dissolved in 30 ml of distilled water, the solution was cooled to 0° C., 0.3 ml of bromine was added, and the mixture was stirred at room temperature for 17 hours while it was shielded from light. After confirmation of disappearance of maltopentaose by TLC (developing solvent: n-butanol:ethanol:water=5:3:2), air was blown into the reaction mixture for removing the excess bromine, and 300 mg of sodium sulfite was further added. The resultant mixture was adjusted to pH 6.17 with 2N sodium hydroxide, 6,658.5 units (6.9 mg as protein) of β-amylase (EC 3.2.1.2; obtained from Sigma; derived from sweet potato) was added, and the reaction was carried out at 40° C. for 2 hours. After confirmation of maltose formation by TLC, the reaction mixture was treated with a bench-top desalting apparatus(Asahi Chemical Industry Microacilyzer Model G1) using a separating membrane of Aciplex cartridge AC-220-10. The yield of maltose was determined by HPLC and found to be 80.3 mg. Upon TLC analysis, this product gave a single spot.

EXAMPLE 4

Maltopentaose (0.25 mmol, 207.18 mg; obtained from Hayashibara Biochemical Laboratories; at least 98% pure), 20 mmol (1.54 g) of ammonium acetate and 10 mmol (630 mg) of sodium cyanoborohydride were dissolved in 10 ml of a methanol solution (methanol:distilled water=9:1 by volume), and the reaction was carried out at ordinary temperature for 40 hours. After addition of 6.5 ml of 6N hydrochloric acid, the reaction mixture was desalted with a bench-top desalting apparatus (Asahi Chemical Industry Microacilyzer Model G1) using a separating membrane of Aciplex cartridge AC-220-10. The sample solution was adjusted to a volume of 50 ml with distilled water and applied to a column (20 mm φ×30 cm) packed with a strongly acidic ion exchange resin (Dowex 50WX2, H$^+$ form). After washing with 300 ml of distilled water, elution was carried out with 300 ml of ammonia water and the eluate was collected and concentrated under reduced pressure.

To this solution (6 ml, pH 9.05) was added 6,658.5 units (6.9 mg as protein) of β-amylase (EC 3.2.1.2; obtained from Sigma; derived from sweet potato), and incubation was carried out at 40° C. for 120 minutes. After confirmation of maltose formation by TLC, the sample solution was adjusted to a volume of 50 ml with distilled water and again subjected to resin treatment under the same conditions as mentioned above. The effluent fraction was regarded as an unadsorbed fraction. The column was washed with water and the eluate was fractionated in 100 ml portions. Each fraction was treated with the above-mentioned Microacylizer evaporated to dryness under reduced pressure and dissolved in 1 ml of distilled water and subjected to TLC analysis, whereby it was found that the effluent fraction and the first 100 ml eluate fraction contained the desired product maltose. Both the fractions were combined and evaporated to dryness under reduced pressure to give 66.1 mg of maltose. The yield was 78.4%. Upon TLC analysis, this product gave a single spot.

EXAMPLE 5

In 100 ml of distilled water was dissolved with heating 3 g of amylose A (obtained from Nakalai Tesque; derived from corn starch, average molecular weight 2,900). After cooling, 1 ml of bromine was added, and the mixture was stirred at room temperature for 2 days while it was shielded from light. The excess bromine was removed by blowing air into the mixture, and the mixture was further stirred until disappearance of the color thereof. The mixture was applied to 200 ml of a strongly basic ion exchange resin (Diaion SA-10A, OH$^-$ form) and, after washing with 2,000 ml of water, carboxylic acid derivatives were eluted with 2,000 ml of 0.5N hydrochloric acid. The eluate was neutralized with KOH, then desalted with a bench-top desalting apparatus (Asahi Chemical Industry Microacilyzer Model G3) using a separating membrane of Aciplex cartridge AC-220-400 and concentrated under reduced pressure. The concentrate was lyophilized to give 1.40 g of a powder. A 200 mg portion of this powder was weighed and dissolved in 10 ml of 20 mM acetate buffer (pH 4.8) with heating and, after cooling, 2,219.5 units (2.3 mg as protein) of β-amylase (obtained from Sigma; derived from sweet potato) was added. The mixture was incubated at 40° C. for 3 hours, then the insoluble matter was removed by centrifugation, and the supernatant was desalted and deprived of β-amylase cleavage residues with a Microacilyzer G1 apparatus using a separating membrane of Aciplex cartridge AC-230-10. Maltose assay by HPLC revealed a yield of 137 mg.

Infusion Fluid Example

Maltotriose (15 g), 0.03 g of potassium chloride, 0.02 g of calcium chloride, 0.6 g of sodium chloride and 0.31 g of sodium lactate are combinedly dissolved in water to give 100 ml of an infusion fluid.

Reference Example 1

Preparation of a maltotriose-forming enzyme

*Streptomyces griseus* NA-468 was inoculated into a medium comprising 3% dextrin, 2% soybean flour, 0.1% yeast extract, 0.1% polypeptone, 0.3% $KH_2PO_4$, 0.5% $CaCl_2$ and 0.1% $(NH_4)_2SO_4$ (pH 7.0) and shake-cultured at 27° C. for 4 days. Ammonium sulfate was added to the culture supernatant to 40–60% saturation. The resultant precipitate fraction was collected and dialyzed against 0.01M acetate buffer (pH 5.8), the dialyzate was subjected to centrifugation, and the supernatant was used as a maltotriose-forming enzyme preparation.

Reference Example 2

Preparation of a maltotetraose-forming enzyme

*Pseudomonas stutzeri* IFO 3773 was inoculated into a medium comprising 1.0% Bacto-casitone, 0.5% yeast extract, 0.28% $KH_2PO_4$ and 0.1% $K_2HPO_4$ (pH 7.0) and cultured at 30° C. for 18 hours. The culture supernatant was partially purified by precipitation with ammonium sulfate followed by dialysis and used as a maltotetraose-forming enzyme preparation.

Reference Example 3

Preparation of a 5% palladium-carbon catalyst $PdCl_2$ (320 mg) was dissolved in concentrated hydrochloric acid (5 ml), and distilled water (30 ml) and active carbon (Shirasagi Z; 3.8 g) were added. The mixture was adjusted to pH 5.0 with 10N sodium hydroxide and, then, an aqueous solution prepared by dissolving $NaBH_4$ (341 mg) in distilled water (10 ml) was added quickly. The resultant mixture was filtered, and the solid was washed with water and used as a 5% palladium-carbon catalyst.

EXAMPLE 6

Potato starch was treated with α-amylase and pullulanase. To the thus-obtained solution (198 mg/20 ml) was added 4 ml of a phenylhydrazine solution (phenylhydrazine:acetic acid:water=2:1:1 by volume), and the mixture was heated on a boiling water bath for 90 minutes, then allowed to cool, made weakly alkaline by addition of 17 ml of 1M sodium carbonate and extracted three times with an equal volume of ethyl acetate. The aqueous layer was desalted with a bench-top desalting apparatus (Asahi Chemical Industry Microacilyzer Model G1) using a separating membrane of Aciplex cartridge AC-220-10. To this starch osazone solution (pH 7.6) was added 6,660 units (6.9 mg as protein) of β-amylase (obtained from Sigma; derived from sweet potato), and incubation was carried out at 40° C. for 60 minutes. After confirmation of maltose formation by TLC, the reaction mixture was ice-cooled and the resultant precipitate was removed by centrifugation. The supernatant was applied to a column packed with 100 ml of a strongly acidic cation exchange resin (Dowex 50WX2, $H^+$ form). The efficient fraction and an initial wash fraction, which were found to contain maltose, were collected. Maltose, which gave a single spot upon TLC analysis, was obtained in a yield of 75.7 mg or 38.2%.

EXAMPLE 7

Corn starch (30 g) was dissolved in 70 ml of distilled water, and 1 ml of 1M calcium chloride was added. After further addition of 2,400 units (2.4 mg as protein) of α-amylase (obtained from Sigma; derived from *Bacillus licheniformis*), the mixture was incubated at 85° C. for 50 minutes. After terminating the reaction by autoclaving, pullulanase (obtained from Hayashibara; derived from *Klebsiella pneumoniae*) was added in an amount of 3.5 mg as protein and incubation was performed at 50° C. for 20 hours. To a 8 ml portion of this liquefied starch solution was added 160 µl of bromine, and the mixture was stirred at room temperature for 70 hours while it was shielded from light. Air was blown into the mixture for removing bromine, the mixture was adjusted to pH 6.0 with a sodium hydroxide solution, 48 units (50 µg as protein) of β-amylase (obtained from Sigma; derived from sweet potato) was added, and the mixture was incubated at 40° C. for 24 hours. The purity as determined by HPLC was 96% and the yield was 61%.

EXAMPLE 8

Potato starch (15 g) was suspended in 135 ml of distilled water, 2.5 µl (=75µg of protein, 75 units) of α-amylase (obtained from Sigma; derived from *Bacillus licheniformis*) was added, and the mixture was stirred vigorously at 85° C. for 20 minutes. Then the reaction was terminated by autoclaving and, after cooling, 1 ml (4.1 mg as protein) of a pullulanase solution (obtained from Hayashibara) was added, and the mixture was incubated at 50° C. for 4 hours. After cooling, 2 ml of bromine was added and the mixture was stirred at room temperature for 2 days while it was shielded from light. Then air was blown into the mixture for bromine removal, and the mixture was neutralized with sodium hydroxide and desalted with a bench-top desalting apparatus (Asahi Chemical Industry Microacilyzer Model G3) using a separating membrane of Aciplex cartridge AC-220-400 to give a 24.4 mg/ml liquefied and oxidized starch solution. A 10 ml portion of this solution was taken, 20 µl (185 µg as protein) of β-amylase (obtained from Nagase Sangyo; derived from soybean) was added, and the mixture was incubated at 40° C. for 22 hours. The reaction mixture was subjected to desalting with a bench-top desalting apparatus (Asahi Chemical Industry Microacilyzer Model S1) using a separating membrane of Aciplex cartridge AC-220-10 and treatment with active carbon and then assayed for maltose by HPLC. The yield of maltose was found to be 113 mg or 46.3%. The purity was 98.7%.

EXAMPLE 9

In 4 ml of distilled water was dissolved 200 mg of Fuji-Oligo 6.7 (obtained from Nihon Shokuhin Kako), followed by addition of 3.6 g of 2-aminopyridine, 1.6 ml of acetic acid and 14.4 ml of methanol. After the solution became homogeneous, 1.4 g of sodium cyanoborohydride was added and the reaction was carried out at 75° C. for 75 hours. After addition of 8 ml of 6 N hydrochloric acid, the reaction mixture was desalted with a bench-top desalting apparatus (Asahi Chemical Industry Microacilyzer Model G1) using a separating membrane of Aciplex cartridge AC-220-10. The desalted mixture was then applied to a strongly acidic cation exchange resin (Dowex 50WX2 $H^+$ form, 25 ml). After washing with water, elution was carried out using 150 ml of 1N ammonia water and the eluate fractions were combined, evaporated to dryness and then redissolved in 5 ml of water. The solution was adjusted to pH 6.0. To the solution was added 53 units (1.2 mg as protein) of the maltotriose-forming enzyme prepared as described in Reference Example 1, and incubation was performed at 40° C. for 4 hours. After confirmation of maltotriose formation by TLC, the incubation mixture was subjected again to the same ion exchange resin treatment as mentioned above. The unadsorbed (effluent) fraction and the early wash fractions were combined and again desalted to give 20 mg of maltotriose. This product gave a single spot in TLC and had a purity of 89% as determined by HPLC.

EXAMPLE 10

In 1 ml of distilled water was dissolved 227 mg of San-Oligo 5.6 (obtained from Sanmatsu Kogyo), followed by addition of 100 μl of 2N sodium hydroxide and 1.5 g of ammonium acetate. After the solution became homogeneous, methanol was added, then 630 mg of sodium cyanoborohydride was added, and the reaction was performed at room temperature for 62 hours. The reaction mixture was neutralized with 6N hydrochloric acid, then desalted with a bench-top desalting apparatus (Asahi Chemical Industry Microacilyzer Model G1) using a separating membrane of Aciplex cartridge AC-220-10 and applied to 50 ml of a strongly acidic cation exchange resin (Dowex 50WX2, $H^+$ form) for adsorption. After washing the resin with water, elution was carried out using 300 ml of 1N ammonia. The eluate fractions were combined, evaporated to dryness, and redissolved in 5 ml of water. The solution was adjusted to pH 6.0. To the solution was added 53 units (1.2 mg as protein) of the maltotriose forming enzyme prepared as described in Reference Example 1, and incubation was conducted at 40° C. for 2 hours. After confirmation of maltotriose formation, the reaction mixture was subjected to the same resin treatment as mentioned above. The unadsorbed fraction and the early wash fractions were combined and again subjected to desalting to give 55.7 mg of maltotriose, which was found to be 97% pure upon HPLC.

EXAMPLE 11

In 9.3 ml of distilled water was dissolved 720 mg of reducing endoxidized liquefied starch prepared by the procedure described in Example 8 using potato as the starting material. To the solution were added 500 μl of 0.5M acetate buffer (pH 6.0, containing 0.1M $CaCl_2$) and 250 μl of the maltotetraose-forming enzyme prepared as described in Reference Example 2, and the reaction was carried out at 30° C. HPLC analysis revealed a purity of 84.8% and a yield of 45.6%.

EXAMPLE 12

San-Oligo 5.6 (10 g, obtained from Sanmatsu Kogyo) was dissolved in 190 ml of distilled water, the whole amount of 5% palladium carbon prepared as described in Reference Example 3 was added, and air was blown into the mixture at a rate of 41 ml/minute for 13 hours with stirring while the temperature was maintained at 50° C. and the pH at 9 to 10 with 10N sodium hydroxide. The reaction mixture was filtered and the filter was washed with water. The filtrate and washings were combined and concentrated to 200 ml and then adjusted to pH 4.0. β-amylase (obtained from Nagase Sangyo; derived from soybean; 500 μl, 1,670 units) was added and the reaction was conducted at 40° C. for 7 hours. The reaction mixture was treated on a bench-top desalting apparatus (Asahi Chemical Industry Microacilyzer Model G3) using a separating membrane of Aciplex cartridge AC-220-400 for desalting and removal of β-amylase cleavage residues. HPLC analysis revealed formation of 2.4 g of maltose.

The purity was 92.5%.

Separately, unoxidized San-Oligo 5.6 was treated with β-amylase in the same manner. The purity of maltose was 70%.

EXAMPLE 13

Bromine (88 mg) was dissolved in 10 ml of 0.2 N NaOH and the pH was adjusted to 13 with 10N NaOH. Maltopentaose (0.46 g; obtained from Seikagaku Kogyo) was added, the vessel was closed with a ground stopper, and the mixture was stirred overnight at room temperature. The reaction mixture was desalted by electrodialysis (Asahi Chemical Industry's Microacilyzer Model S1, Aciplex cartridge AC-110-10), then 0.5 ml of 0.2M acetate buffer (pH 5.0) and 0.5 ml of the same β-amylase as used in Example 12, and the reaction was conducted overnight at 40° C. HPLC analysis of the reaction mixture revealed a maltose purity of 97.1% and a yield of 36.9% (theoretical yield 43.5%).

EXAMPLE 14

Corn starch (4.5 kg) was suspended in 10.35 liters of distilled water and 150 ml of 1M $CaCl_2.2H_2O$ to give 30% (w/w) starch milk, 12 ml of β-amylase (obtained from Sigma; derived from *Bacillus licheniformis*; 80 units per gram of corn starch being added) was added, and liquefaction was effected at 90° C. for 50 minutes. (This liquid had a D.E. value of 3.7) The mixture was then subjected to autoclaving at 121° C. for 10 minutes for β-amylase deactivation. Then, 320 ml (17.78 units per gram of corn starch) of pullulanase DE-250 (obtained from Amano Pharmaceutical) was added and the reaction was carried out at 50° to 55° C. for 16 hours. (The D.E. value was then 8.2.) A 5 ml portion of the reaction mixture was taken and diluted with 5 ml of water. To this was added a two-fold dilution (diluent: water; pH adjusted to 11.1) of 1.25 ml of a sodium hypochlorite solution with an effective chlorine concentration of about 8.5 to 13.5% (Antiformin, Nakarai Chemical) while the pH was maintained at 11.05 to 11.25 with 1N NaOH and the liquid temperature at 40° C. The reaction was then conducted at 40° C. for 2 hours. Then, 200 mg of sodium sulfite was added, and the resultant mixture was stirred for 5 minutes and adjusted to pH 6.54 with 3N hydrochloric acid. This liquid was treated on an electrodialyzer (Asahi chemical Industry's Microacilyzer Model S1, Aciplex cartridge AC-110-10) and then adjusted to pH 5 to 6, 0.5 ml of the same β-amylase as used in Example 12 was added, and the reaction was conducted at 40° C. for 18 hours. The precipitate in the reaction mixture was removed by centrifugation, the supernatant was subjected to ultrafiltration (Millipore, Ultrafree C3LCC) and the filtrate was analyzed by HPLC. The purity of the product maltose was found to be 95.6% and the yield 67.8%.

EXAMPLE 15

A 20 ml portion of the 30% (w/w) corn starch liquefaction mixture (D.E. value 8.2) obtained in Example 14 was taken and adjusted to pH 11.5 by addition of 0.1 ml of 10N NaOH. To this was added dropwise and gradually 4 ml of a sodium hypochlorite solution with an effective chlorine content of 8.5 to 13.5% (Antiformin, Nakarai Chemical) while the liquid temperature was maintained at 26° C. and the pH at 11.1 to 11.6 with 3N NaOH. Then, the reaction was conducted at 26° C. for 5 hours. The reaction mixture was subjected to β-amylase treatment in the same manner as in Example 14 to give a reaction mixture with a maltose purity of 99.1%. The yield was 37.8%.

EXAMPLE 16

A 20 ml portion of the 30% (w/w) corn starch liquefaction mixture (D.E. value 8.2) obtained in Example 14 was taken and adjusted to pH 10.7 by addition of 0.1 ml of 10N NaOH. To this was added dropwise and gradually 4 ml of a sodium hypochlorite solution with an effective chlorine content of 8.5 to 13.5% (Antiformin, Nakarai Chemical) while the liquid temperature was maintained at 40° C. and the pH at 10.7 to 11.4 with 10N NaOH. Then, the reaction was conducted at 40° C. for 3 hours. The reaction mixture was adjusted to pH 5.8 with concentrated hydrochloric acid, 1.2 ml of the same β-amylase as used in Example 12, and the reaction was conducted at 40° C. for 18 hours to give a reaction mixture with a maltose purity of 99.3%. The yield was 55.7%.

EXAMPLE 17

A 20 ml portion of the 30% (w/w) corn starch liquefaction mixture (D.E. value 8.2) obtained in Example 14 was taken and adjusted to pH 10.7 by addition of 0.1 ml of 10N NaOH. To this was added dropwise and gradually 4 ml of a sodium hypochlorite solution with an effective chlorine content of 8.5 to 13.5% (Antiformin, Nakarai Chemical) while the liquid temperature was maintained at 40° C. and the pH at 10.7 to 11.4 with 10N NaOH. Then, the reaction was conducted at 40° C. for 3 hours. The reaction mixture was adjusted to pH 5.8 with concentrated hydrochloric acid, 1.2 ml of the same β-amylase as used in Example 12 and 0.1 ml of the same pullulanase as used in Example 12 were simultaneously added, and the reaction was conducted at 55° C. for 3 hours to give a reaction mixture with a maltose purity of 99.0%. The yield was 71.9%.

EXAMPLE 18

A 2 g portion of a lyophilizate derived from the oxidized liquefied starch solution obtained in Example 8 was taken and applied, in an appropriate aqueous solution form, to 3 g of an anion exchange resin (Dowex 1x2, OH⁻ form) for adsorption. The column was washed with water thoroughly. Each milliliter of the resin adsorbed 251 mg of the oxidized liquefied starch. A 1.3 ml portion of this resin was packed into a jacketed column (φ9 mm×12 cm) and 5 ml of water and 8 μl of the same β-amylase as used in Example 12 were charged for performing the reaction in a recycling manner. After 5 hours of reaction at 40° C. in that manner, the reaction mixture was collected. Maltose was obtained in a yield of 108 mg (43%) with a purity of 100.0% as determined by HPLC analysis.

EXAMPLE 19

A corn starch liquefaction product was oxidized with 5% sodium hypochlorite according to the procedure of Example 17. The oxidation mixture was applied to an electrodialyzer (Asahi Chemical Industry's Microacilyzer Model S1, Aciplex cartridge AC-110-10) and further to the ion exchange resin Dowex (1x2, OH⁻ form) for sufficient adsorption, whereby each milliliter of the resin adsorbed 112 mg of the above oxidation product. One milliliter of this resin was packed into the same jacketed column as used in Example 18 and treated with β-amylase in the same manner for maltose production, whereby 25 mg of 99.6% pure maltose was obtained.

EXAMPLE 20

Oxidised liquefied starch solution prepared according to the procedure of Example 8 was sufficiently applied to an anion exchange resin (Dowex 1x2, OH⁻ form) for adsorption. Each milliliter of the resin adsorbed 233 mg of the oxidized liquefied starch. A 1 ml portion of this resin was packed into a jacketed column according to the precedure of Example 18, and 1.3 mg of glucoamylase from *Rhizopus niveus* (Seikagaku Kogyo, 39.4 U/mg) was charged for performing the reaction in a recycling manner. After 16 hours of reaction at 40° C. in that manner, the reaction mixture was collected. Glucose was obtained in a yield of 55 mg with a purity of 100.0% as determined by HPLC analysis.

What is claimed is:

1. A process for producing a desired saccharide of a predetermined, definite chain length which comprises subjecting a saccharide having a chain length larger than said definite chain length or mixture of such saccharides to modification of the hydroxy group carried by the anomeric carbon atom at the reducing end thereof without using any transglycosidase, and without modifying the non-reducing end thereof, then repeatedly cleaving the modified saccharide by treating the modified saccharide with an enzyme capable of repeatedly cleaving a saccharide chain of said predetermined definite chain length in an exo manner therefrom to produce said desired saccharide of predetermined definite chain length and recovering said desired saccharide.

2. A process for producing saccharides as claimed in claim 1, wherein the modification at the reducing end of the starting saccharides comprises oxidizing the reducing end of the saccharide having an arbitrary chain length or said mixture.

3. A process for producing a saccharide as claimed in claim 2, wherein the oxidizing of the reducing end of the saccharide is the conversion of the anomeric carbon atom at the reducing end thereof to a carboxylic group.

4. A process for producing desired saccharides of a predetermined definite chain length which comprises subjecting a saccharide having a chain length larger than said definite chain length or mixture of such saccharides to modification of the hydroxy group carried by the anomeric carbon atom at the reducing end thereof without using any transglycosidase, and without modifying the non-reducing end thereof, then causing the modified saccharide to be absorbed on an ion exchange resin, then repeatedly cleaving said modified saccharide by treating said modified saccharide with an enzyme capable of repeatedly cleaving a saccharide chain of said predetermined definite chain length in an exo manner therefrom to produce said desired saccharide of predetermined definite chain length and recovering said desired saccharide of predetermined definite chain length from said ion exchange resin.

5. A process for producing saccharides as claimed in claim 4, wherein the modification at the reducing end of the starting saccharide comprises oxidizing the reducing end of said saccharide having an arbitrary chain length or said mixture.

6. A process for producing a saccharide as claimed in claim 5, wherein the oxidizing of the reducing end of said saccharide is the conversion of the anomeric carbon atom at the reducing end thereof to a carboxylic group.

* * * * *